(12) United States Patent
Benneker et al.

(10) Patent No.: US 7,161,037 B2
(45) Date of Patent: Jan. 9, 2007

(54) PROCESS FOR TREATING AN AQUEOUS MEDIUM CONTAINING PHOSPHATE SALT AND ORGANIC COMPOUNDS

(75) Inventors: Arno Herald Benneker, Doenrade (NL); Hendrik Oevering, Elsloo (NL); Johannes Antonius Leonardus Brouwers, Echt (NL)

(73) Assignee: DSM IP Assets B.V. (NL)

( * ) Notice: Subject to any disclaimer, the term of this patent is extended or adjusted under 35 U.S.C. 154(b) by 118 days.

(21) Appl. No.: 10/497,230

(22) PCT Filed: Dec. 2, 2002

(86) PCT No.: PCT/NL02/00780

§ 371 (c)(1),
(2), (4) Date: Nov. 17, 2004

(87) PCT Pub. No.: WO03/048037

PCT Pub. Date: Jun. 12, 2003

(65) Prior Publication Data

US 2005/0070739 A1    Mar. 31, 2005

(30) Foreign Application Priority Data

Dec. 4, 2001 (EP) ................................ 01204697

(51) Int. Cl.
*C01B 21/38* (2006.01)
*C07C 249/08* (2006.01)

(52) U.S. Cl. .................................. 564/259; 423/390.1
(58) Field of Classification Search ................ 564/259; 423/390.1
See application file for complete search history.

(56) References Cited

U.S. PATENT DOCUMENTS

| 3,940,442 A | * | 2/1976 | de Rooij | ..................... 564/259 |
| 3,948,988 A | | 4/1976 | De Rooij | |
| 3,997,607 A | * | 12/1976 | de Rooij | ..................... 564/259 |

FOREIGN PATENT DOCUMENTS

| GB | 1138750 | 1/1969 |
| GB | 1284515 | 4/1971 |

* cited by examiner

*Primary Examiner*—Thurman K. Page
*Assistant Examiner*—Chukwuma Nwaonicha
(74) *Attorney, Agent, or Firm*—Nixon & Vanderhye, PC

(57) ABSTRACT

The invention relates to a process for preparing nitric acid by treating an aqueous medium containing organic compounds and phosphate, said process comprising:
feeding the aqueous medium to a nitric acid synthesis zone;
forming nitric acid by contacting the aqueous medium with a gaseous medium in said nitric acid synthesis zone, said gaseous medium containing $NO_2$;
discharging an off-gas from said nitric acid synthesis zone;
wherein the total organic carbon concentration in the aqueous medium entering the nitric acid synthesis zone is less than 0.03 wt. %.

10 Claims, 1 Drawing Sheet

PROCESS FOR TREATING AN AQUEOUS MEDIUM CONTAINING PHOSPHATE SALT AND ORGANIC COMPOUNDS

CROSS REFERENCE TO RELATED APPLICATION

This application is the National Phase of International Application PCT/NL02/00780 filed Dec. 2, 2002 which designated the U.S., and was published in the English language.

The invention relates to a process for treating an aqueous medium containing organic compounds and phosphate to prepare nitric acid. The invention also relates to a process for preparing cyclohexanone oxime.

Oximes can be produced in a process in which a buffered, aqueous medium containing buffer acids or acidic salts, for example phosphate buffers, and buffer salts derived from these acids, is continuously recycled between a hydroxylammonium synthesis zone, in which nitrate ions are catalytically reduced with molecular hydrogen to hydroxylammonium, and an oximation zone where a ketone, e.g. cyclohexanone, is converted to an oxime. After having been enriched in hydroxylammonium in the hydroxylammonium synthesis zone, the aqueous medium is then passed to the oxime synthesis zone, where the hydroxylammonium reacts with a ketone, e.g., cyclohexanone, forming the corresponding oxime. The oxime can then be separated from the aqueous medium which is recycled to the hydroxylammonium synthesis zone.

The net chemical reactions occurring during the process can be represented by the following equations:

1) Preparation of the hydroxylammonium:

$$2H_3PO_4 + NO_3^- + 3H_2 \rightarrow NH_3OH^+ + 2H_2PO_4^- + 2H_2O$$

2) Preparation of the oxime

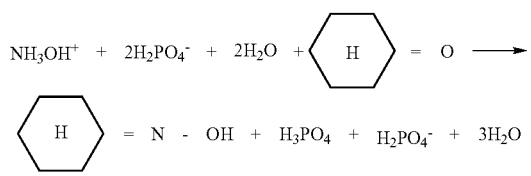

3) Supply of $HNO_3$ to make up the depletion of the source of nitrate ions after removal of the oxime formed

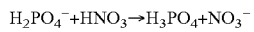

$$H_2PO_4^- + HNO_3 \rightarrow H_3PO_4 + NO_3^-$$

Before the aqueous medium is passed into the hydroxylammonium synthesis zone, it may be enriched with the required nitrate ions by addition of nitric acid or by absorption of nitrous gases in the aqueous medium in which instance nitric acid is formed in situ.

U.S. Pat. No. 3,997,607 describes a process in which the aqueous medium exiting the oxime synthesis zone, and containing 400 ppm (0.040 wt. %) of organic compounds calculated as carbon, is fed into an absorption column in which it is contacted with nitrous gases resulting in the formation of $HNO_3$. An off-gas discharges from the column.

Disadvantage of the process of U.S. Pat. No. 3,997,607 is that there is a high tendency for corrosion of materials which are in contact with the off-gas, presumably due to entrainment of salt in the off-gas.

Goal of the invention is to provide a process wherein the corrosion problems do not occur or occur at least to a lesser extent.

This goal is achieved according to invention by providing a process for treating an aqueous medium containing organic compounds and phosphate to prepare nitric acid, said process comprising:

feeding the aqueous medium to a nitric acid synthesis zone;

forming nitric acid by contacting the aqueous medium with a gaseous medium in said nitric acid synthesis zone, said gaseous medium containing $NO_2$;

discharging an off-gas from said nitric acid synthesis zone;

characterized in that the total organic carbon concentration (TOC) in the aqueous medium entering the nitric acid synthesis zone is less than 0.03 wt. %.

The invention also provides a process for preparing cyclohexanone oxime, said process comprising:

passing an aqueous medium containing phosphate from a hydroxylammonium synthesis zone to a cyclohexanone oxime synthesis zone, from the cyclohexanone oxime synthesis zone to a nitric acid synthesis zone, and from the nitric acid synthesis zone to the hydroxylammonium synthesis zone;

preparing hydroxylammonium by catalytically reducing nitrate with hydrogen in said hydroxylammonium synthesis zone;

preparing cyclohexanone oxime by reacting hydroxylammonium with cyclohexanone in said cyclohexanone oxime synthesis zone;

forming nitric acid by contacting the aqueous medium with a gaseous medium in said nitric acid synthesis zone, said gaseous medium containing $NO_2$;

discharging an off-gas from said nitric acid synthesis zone; characterized in that the total organic carbon concentration (TOC) in the aqueous medium entering the nitric acid synthesis zone is less than 0.03 wt. %.

According to the invention the tendency for corrosion is decreased. This increase the lifetime of materials which are in contact with the off-gas. It is also possible to apply materials which are less corrosion resistant, with no increase of corrosion problems.

According to the invention the total organic carbon concentration (TOC) in the aqueous medium entering the nitric acid synthesis zone is less than 0.03 wt. %. As used herein the total organic carbon concentration (TOC) refers to the sum concentration of all organic compounds, calculated as carbon. The TOC may be determined by known methods, for instance by oxidizing the organic compounds to $CO_2$ and determining the amount of $CO_2$ formed. Preferably, the total organic carbon concentration (TOC) in the aqueous medium entering the nitric acid synthesis zone is less than 0.020 wt. %, more preferably less than 0.015 wt. %, most preferably less than 0.010 wt. %. This further reduces the severity of the corrosion conditions for materials which are in contact with the off-gas.

As used herein, concentrations in the aqueous medium entering the nitric acid synthesis zone, refer to the concentrations in the aqueous medium which is fed to the nitric acid synthesis zone. The weight percentages are given with respect to the weight of the aqueous medium which is fed to the nitric acid synthesis zone.

According to the invention nitric acid is formed in the nitric acid synthesis zone by contacting the aqueous medium with a gaseous medium, said gaseous medium containing $NO_2$; In a preferred embodiment, the gaseous medium also comprises NO and $O_2$.

The formation of nitric acid can be represented by the following equation:

4) $3NO_2 + H_2O \rightarrow 2HNO_3 + NO$

Nitrogen dioxide may be formed according to the following equation:

5) $2NO + O_2 \rightarrow 2NO_2$

The aqueous medium may be contacted with the gaseous medium by any suitable method. Preferably, the aqueous medium and the gaseous medium are contacted in countercurrent flow. Preferably, the superficial gas velocity of the gaseous medium in the nitric acid synthesis zone is between 0.05 and 1 m/s, more preferably between 0.1 and 0.5 m/s. Applying a superficial gas velocity below the upper preferred values further reduces the occurrence of corrosion problems. As used herein the superficial gas velocity refers to the volumetric flow (in $m^3/s$) of the gaseous medium divided by the free cross sectional area of the nitric acid synthesis zone (in $m^2$). The temperature in the nitric acid synthesis zone is generally between 10 and 100° C., preferably below 60° C. The pressure in the nitric acid synthesis zone is generally between 1 and 20 MPa. Any suitable vessel may be used as a nitric acid synthesis zone. Preferably, the nitric acid synthesis zone is a column. Preferably, such column is a plate column or a packed column. The plate column may be any suitable column fitted with plates, for instance sieve trays, bubble caps or valve trays.

The gases to be reacted may be fed to the nitric acid synthesis zone by any suitable method or may be formed in situ. $NO_2$, and preferably also $O_2$, may be fed to the nitric acid synthesis zone. It is also possible to feed NO and $O_2$, and optionally $NO_2$, to the nitric acid synthesis zone. $O_2$ may be fed to the nitric acid synthesis zone by feeding air. The abovementioned gaseous compounds may be fed to the reaction zone separately, or as a mixture. In a preferred embodiment the gases entering the nitric acid synthesis zone originate from an ammonium destruction zone, in which ammonium is reacted with nitrous gases.

The off-gas may comprise any type of nitrous compounds, for instance NO and/or $NO_2$. The off-gas may also contain $N_2O_3$, and/or $N_2O_4$. The off-gas may also contain one or more inert gases, for instance $N_2$.

The aqueous medium contains phosphate, preferably between 2.0–8.0 mol phosphate per liter of aqueous medium. The phosphate may be present as $H_3PO_4$, $H_2PO_4^-$, $HPO_4^{2-}$ and/or $PO_4^{3-}$. Preferably, the aqueous medium is buffered. Preferably, the aqueous medium is an acidic aqueous medium. Preferably, the aqueous medium entering the nitric acid synthesis zone has a pH of between 0 and 4, more preferably between 0.5 and 4. In a preferred embodiment, the aqueous medium entering the nitric acid synthesis zone contains 2.0–8.0 mol phosphate, 0.5–8.0 mol ammonium ($NH_4^+$) and 0.1–5.0 mol nitrate ($NO_3^-$) per liter of aqueous medium. As used herein the phosphate content refers to the joint content of $H_3PO_4$, $H_2PO_4^-$, $HPO_4^{2-}$ and $PO_4^{3-}$ per liter of aqueous medium. The aqueous medium comprises organic compounds. Examples of organic compounds include cyclohexanone, cyclohexanone oxime, cyclohexylamine, carboxylic acids, and/or amine compounds. Preferably, the joint content of (sum concentration of) cyclohexanone and cyclohexanone oxime entering the nitric acid synthesis zone is less than 0.001 wt. %, more preferably less than 0.0005 wt. %, most preferably less than 0.0002 wt. %. These weight percentages are given relative to the weight of the aqueous medium.

The aqueous medium may be discharged from the nitric acid synthesis zone by any suitable method. Preferably, the aqueous medium leaving the nitric acid synthesis zone comprises between 1 and 8 mol nitrate per liter of aqueous medium.

Preferably, the process comprises separating organic compounds from said aqueous medium prior to feeding said aqueous medium to said nitric acid synthesis zone. Preferably, said separating is carried out by stripping, e.g. by a process as described in U.S. Pat. No. 3,940,442. In a preferred embodiment the stripping comprises feeding the aqueous medium to a stripping zone; passing steam through the aqueous medium in the stripping zone; and discharging a vapour stream comprising steam and organic compounds from said stripping zone. The aqueous medium and the steam may be contacted by any suitable method. Preferably, the aqueous medium and the steam are contacted in countercurrent flow. Preferably, the superficial gas velocity of said steam passing through the stripping zone is between 0.2 and 3 m/s, more preferably between 0.4 and 1.5 m/s. As used herein the superficial gas velocity refers to the volumetric steam flow (in $m^3/s$) divided by the free cross sectional area (perpendicular to the direction of steam flow) of the stripping zone (in $m^2$). Preferably, the temperature in the stripping zone is between 90–180° C., more preferably between 105 to 160° C. The pressure in the stripping zone may be atmospheric. Preferably, the pressure in the stripping zone is between 0.05 to 1 MPa, more preferably between 0.09 to 0.6 MPa. Preferably, the residence time of the aqueous medium in the stripping zone is between 0.5 and 60 minutes. Any suitable vessel may be used as a stripping zone. Preferably, the stripping zone is a column. Preferably, such column is a plate column or a packed column. The plate column may be any suitable column fitted with plates, for instance sieve trays, bubble caps or valve trays. Preferably, the stripping is carried out in a stripping zone such that the TOC in the aqueous medium leaving the stripping zone is less than 0.030 wt. %, preferably less than 0.020 wt. %, more preferably less than 0.015 wt. %, more preferably less than 0.010 wt. %.

In the cyclohexanone oxime synthesis zone, hydroxylammonium is reacted with cyclohexanone to form cyclohexanone oxime, preferably in the presence of an organic solvent. Any suitable organic solvent may be used in which cyclohexanone and cyclohexanone oxime may be dissolved. Preferably, the organic solvent is selected from the group consisting of benzene, toluene, xylene, methylcyclopentane, cyclohexane and mixtures thereof. Most preferably, the organic solvent is toluene. A suitable process is for instance described in GB-A-1,138,750. In a preferred embodiment, the reaction of hydroxylammonium with cyclohexanone is effected by contacting the aqueous medium and an organic stream comprising cyclohexanone and the organic solvent in countercurrent flow. The cyclohexanone oxime produced may be discharged from the cyclohexanone oxime synthesis zone by any suitable method, preferably by withdrawing an organic product from the cyclohexanone oxime synthesis zone, said organic product comprising the cyclohexanone oxime and the organic solvent. The organic solvent and the cyclohexanone may be introduced into the cyclohexanone oxime synthesis zone at any suitable point, preferably downstream of the point where the organic product is withdrawn from the cyclohexaone oxime synthesis zone (seen in the direction of flow of the aqueous medium). Most preferably, the organic solvent and the cyclohexanone are introduced into the cyclohexanone oxime synthesis zone downstream of the point where the organic product is discharged from the cyclohexanone oxime synthesis zone, and the organic solvent is introduced downstream of the point where the cyclohexanone is introduced into the cyclohexanone oxime synthesis zone (seen in the direction of flow of the aqueous medium. This embodiment has the advantage that extraction of residual amounts of cyclohexanone and cyclohexanone oxime is improved. As used herein, the zone between the point where the organic product leaves the cyclohexanone oxime synthesis zone and the point where the cyclohexanone is introduced into the cyclohexanone oxime synthesis zone is also referred to as reaction zone. As used herein the zone between the point where the cyclohexanone is introduced into the cyclohexanone oxime synthesis zone and the point where the organic solvent is introduced into the cyclohexanone oxime synthesis zone is also referred to as extraction zone. For the reaction zone and/or extraction zone, use may be made of known types of counterflow reactors, such as for instance pulsed columns filled with packing bodies or rotating disc reactors. It is also possible to use a system comprising a number, e.g. 3 to 6, of series-connected reactors equipped with stirrers, each of these reactors also being provided with a liquid-liquid separator. The cyclohexanone oxime synthesis zone is preferably operated at a temperature between 40 to 150° C. Preferably, the reaction medium entering the cyclohexanone oxime synthesis zone has a pH of between 1 and 6, more preferably between 1.5 and 4. Preferably, the concentration of hydroxylammonium in the aqueous medium entering (fed to) the cyclohexanone oxime synthesis zone is between 0.8 and 2.5 mol hydroxylammonium per liter of aqueous medium.

In the hydroxylammonium synthesis zone hydroxylammonium is formed by catalytic reduction of nitrate or nitrogen oxide with hydrogen. The hydroxylammonium synthesis zone may be operated at a temperature ranging from 20 to 100° C., preferably 30–90° C., more preferably 40–65° C., and at atmospheric, sub-atmospheric or elevated pressures, preferably between 0.1 and 5 MPa, more preferably between 0.3 and 3 MPa, and in particular between 0.5 and 2 MPa (hydrogen partial pressure). Preferably, the pH in the hydroxylammonium synthesis zone is between 0.5 and 6, more preferably between 1 and 4. The catalyst employed in this zone is generally present in a range of between 1 to 25 wt. %, preferably between 5 to 15 wt. % of a precious metal, relative to total weight of support plus catalyst. Preferably, the catalyst is a palladium containing catalyst, for instance a palladium or a palladium-platinum catalyst, present on a support, such as for instance carbon or alumina support. Generally, the catalyst is present in the hydroxylammonium synthesis zone in an amount of 0.2–5 wt. % relative to the total liquid weight in the hydroxylammonium reactor vessel(s). The hydroxylammonium synthesis zone is not limited to a specific reactor. A reactor with a mechanical stirrer may be used. Preferably, the reactor is column, preferably a bubble column. An example of suitable bubble column is described in NL-A-6908934.

Preferably, the process is a continuous process.

DESCRIPTION OF PREFERRED EMBODIMENTS

Figure 1:
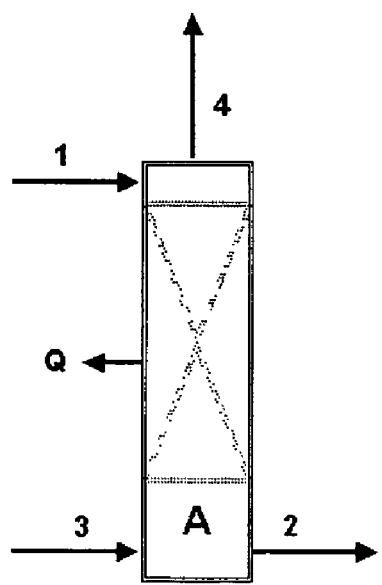
FIG. 1 is a schematic diagram of a preferred embodiment of the process according to the invention.

Referring to FIG. 1, letter A represents the nitric acid synthesis zone, in this case a column fitted with sieve trays. The aqueous medium is fed to the top of column A via line 1. A gas mixture containing NO, $NO_2$, and $O_2$ is fed to the bottom of column A via line 3. Aqueous medium enriched in nitric acid is discharged from column A via line 2. An off-gas is discharged from the column via line 4. The column is cooled.

Figure 2:
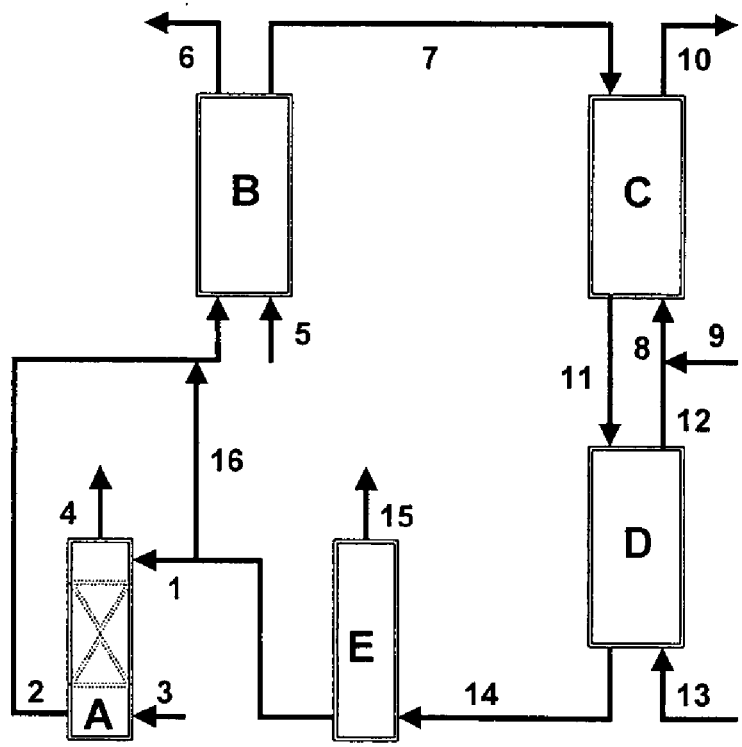
FIG. 2 is a schematic diagram of a preferred embodiment wherein the process according to the invention is part of a process for the production of cyclohexanone oxime.

Referring to FIG. 2, B represents the hydroxylammonium synthesis zone. A cyclohexanone oxime synthesis zone is used comprising reaction zone C and extraction zone D. To zone B, containing catalyst, hydrogen is fed via line 5; unreacted hydrogen is discharged, with any other gases, via line 6. The aqueous medium, containing, inter alia, phosphate, is fed to zone B through line 2 and line 16, and after having been enriched in hydroxylammonium in the hydroxylammonium synthesis zone, the aqueous medium is passed to the cyclohexanone oxime synthesis zone via line 7. The cyclohexanone oxime synthesis zone comprises reaction zone C and extraction zone D. The cyclohexanone to be converted is fed to zone C in an organic solvent via line 8. The cyclohexanone is introduced into the organic solvent via line 9. The largest part of cyclohexanone oxime produced and dissolved in the organic solvent is removed from the system via line 10.

Upon exiting reaction zone C, the aqueous medium is passed to extraction zone D via line 11. Upon exiting reaction zone C, the hydroxylammonium content of the aqueous medium has been reduced by reaction and contains small quantities of cyclohexanone and cyclohexanone oxime. The organic solvent enters extraction zone D through line 13. In extraction zone D, residual cyclohexanone oxime and cyclohexanone is removed from the aqueous medium.

The aqueous medium exits extraction zone D through line 14 which passes the aqueous medium to a separation operation, stripping column E. In this column organic compounds are removed from the aqueous medium via line 15. The total concentration organic compounds (TOC) in the aqueous medium leaving stripping column E is less than 0.03 wt. %. Part of the aqueous medium leaving the column passes through line 1 to nitric acid synthesis zone A. A gas mixture containing gaseous $NO_2$, NO and $O_2$ is fed to nitric acid synthesis zone A via line 3. An off-gas is discharged from nitric acid synthesis zone A via line 4. Another part of the aqueous medium leaving the stripping column E by-passes nitric acid synthesis zone A via line 16 and is recycled to hydroxylammonium synthesis zone B together with the aqueous medium enriched in nitric acid and leaving nitric acid synthesis zone A. The process is carried out continuously.

The following specific examples are to be construed as merely illustrative, and not limitative, of the remainder of the disclosure.

Comparative Experiment A

In this experiment a column is used as indicated in FIG. 1. The diameter is 3 m, the height 34.6 m. The column is provided with 27 sieve trays. To the top of the column an aqueous medium was fed (9.9 $m^3$ per hour) having the following composition:
18% by weight of $H_3PO_4$
18% by weight of $NH_4NO_3$
16% by weight of $NH_4H_2PO_4$
0.8% by weight of hydroxylammonium phosphate
TOC=0.04 wt. %

Balance substantially water.

To the bottom of the column is fed (4.819 m³ per hour) gas in the following quantities:

| | |
|---|---|
| $H_2O$ | 3.2 wt. % |
| NO | 1 wt. % |
| $NO_2$ | 7.8 wt. % |
| $O_2$ | 5.1 wt. % |
| $N_2$ | 82.9 wt. % |

An off-gas having the following composition is discharged from the top of the column:

| | |
|---|---|
| $H_2O$ | 0.8 wt. % |
| NO | 0.05 wt. % |
| $NO_2$ | 0.06 wt. % |
| $O_2$ | 3.4 wt. % |
| $N_2$ | 95.69 wt. % |

The column is operated at a temperature of 40° C. and at a pressure of 0.7 MPa.

During subsequent treatment the off-gas is heated to a temperature of 150° C.

After operation during 1 year, part of the piping (made of AISI 304L steel), which was contacted with the off-gas, has to be replaced due to corrosion.

EXAMPLE 1

Comparative experiment A is repeated with the only difference that the TOC of the aqueous medium entering the column is 0.026 wt. %. The same part of the piping as in experiment A has to be replaced no earlier than after 3 years.

This example shows that due to a decrease of the TOC in the aqueous medium entering the column, the lifetime of equipment which is contacted with the off-gas is increased.

EXAMPLE 2

Example 1 is repeated with the only difference that the TOC of the aqueous medium entering the column is 0.008 wt. %. The same part of the piping as in example 1 has to be replaced no earlier than after 6 years.

This example shows that due to a decrease of the TOC in the aqueous medium entering the column, the lifetime of equipment which is contacted with the off-gas is further increased.

The invention claimed is:

1. Process for preparing nitric acid by treating an aqueous medium containing organic compounds and phosphate, said process comprising:
   feeding the aqueous medium to a nitric acid synthesis zone;
   forming nitric acid by contacting the aqueous medium with a gaseous medium in said nitric acid synthesis zone, said gaseous medium containing $NO_2$;
   discharging an off-gas from said nitric acid synthesis zone;
   wherein the total organic carbon concentration in the aqueous medium entering the nitric acid synthesis zone is less than 0.03 wt. %.

2. Process according to claim 1, wherein the total organic carbon concentration in the aqueous medium entering the nitric acid synthesis zone is less than 0.02 wt. %.

3. Process according to claim 1, wherein the gaseous medium further comprises NO and $O_2$.

4. Process according to claim 1, wherein said nitric acid synthesis zone is a column.

5. Process according to claim 4, wherein said column is a plate column or a packed column.

6. Process according to claim 1, wherein the temperature in the nitric acid synthesis zone is between 10 and 100° C.

7. Process according to claim 1, wherein the process comprises separating organic compounds from said aqueous medium prior to feeding said aqueous medium to said nitric acid synthesis zone.

8. Process according to claim 7, wherein said separating is carried out by stripping.

9. Process according to claim 1, wherein the aqueous medium entering the nitric acid synthesis zone contains between 2.0–8.0 mol/l of phosphate.

10. Process according to claim 1, wherein the off-gas contains $N_2$, NO and/or $NO_2$.

* * * * *